(12) United States Patent
Lee et al.

(10) Patent No.: US 12,702,747 B2
(45) Date of Patent: Aug. 11, 2026

(54) WOUND THERAPY SYSTEM WITH IN-LINE ORIFICE

(71) Applicant: KCI Manufacturing Unlimited Company, Westmeath (IE)

(72) Inventors: Edward Lee, San Antonio, TX (US); Christopher Brian Locke, Bournemouth (GB); Jordan Traxler, San Antonio, TX (US); Elizabeth Trimble, San Antonio, TX (US); Shannon C. Ingram, Bulverde, TX (US); Jessica Snow, San Antonio, TX (US)

(73) Assignee: KCI Manufactuting Unlimited Company, Westmeath (IE)

( * ) Notice: Subject to any disclaimer, the term of this patent is extended or adjusted under 35 U.S.C. 154(b) by 99 days.

(21) Appl. No.: 17/795,077

(22) PCT Filed: Jan. 27, 2021

(86) PCT No.: PCT/IB2021/050619

§ 371 (c)(1),
(2) Date: Jul. 25, 2022

(87) PCT Pub. No.: WO2021/152472

PCT Pub. Date: Aug. 5, 2021

(65) Prior Publication Data

US 2024/0009377 A1 Jan. 11, 2024

Related U.S. Application Data

(60) Provisional application No. 62/967,133, filed on Jan. 29, 2020.

(51) Int. Cl.
*A61M 1/00* (2006.01)

(52) U.S. Cl.
CPC ............ *A61M 1/984* (2021.05); *A61M 1/912* (2021.05); *A61M 1/962* (2021.05); *A61M 1/964* (2021.05); *A61M 1/966* (2021.05)

(58) Field of Classification Search
CPC ...... A61M 1/984; A61M 1/912; A61M 1/962; A61M 1/964; A61M 1/966; A61M 1/96; A61M 1/98; A61B 5/6843
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

International Search Report and Written Opinion Corresponding to Application No. PCT/IB2021/050619, mailed May 31, 2021.

(Continued)

*Primary Examiner* — Jessica Arble
*Assistant Examiner* — Nhu Q. Tran

(57) ABSTRACT

A wound therapy system includes a dressing sealable over a wound, a conduit comprising a first inner diameter, coupled to the dressing, and fluidly communicable with the wound space, and a canister fluidly communicable with the conduit. A therapy unit is coupled to the canister and includes a pump, a sensor configured to measure a pressure, a valve controllable between an open position and a closed position, and a control circuit. The control circuit is configured to control the pneumatic pump to remove air to establish a negative pressure, control the valve to repeatedly alternate (Continued)

between the open closed positions to allow a controlled rate of airflow through the valve, receive measurements of the pressure from the sensor, and determine a volume of the wound space based on the pressure measurements. A portion of the conduit comprises a second inner diameter that is less than the first inner diameter.

10 Claims, 6 Drawing Sheets

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2008/0071235 A1* 3/2008 Locke .................. A61H 9/0057 604/318
2008/0077070 A1* 3/2008 Kopia ................. A61M 1/3653 604/8
2008/0077091 A1* 3/2008 Mulligan ............... G09B 23/28 602/42
2012/0215182 A1* 8/2012 Mansour ............... A61M 39/26 604/256
2014/0163491 A1 6/2014 Schuessler et al.
2015/0032031 A1* 1/2015 Hartwell .............. A61B 5/1073 600/587
2015/0080788 A1 3/2015 Blott et al.
2015/0165182 A1* 6/2015 Pratt ...................... A61M 1/92 604/290
2016/0184496 A1* 6/2016 Jaecklein .............. A61M 1/982 604/318
2018/0042521 A1* 2/2018 Ryu ...................... A61B 5/742
2019/0298579 A1 10/2019 Moore et al.

(56) References Cited

U.S. PATENT DOCUMENTS

| | | | |
|---|---|---|---|
| 2020/0000983 A1* | 1/2020 | Gordon | A61M 1/982 |
| 2021/0268167 A1* | 9/2021 | Rice | A61F 13/00051 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| EP | 2237724 | A1 | 10/2010 |
| EP | 3257438 | A1 | 12/2017 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjöm et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

"D.E. Tribble, An Improved Sump Drain-Irrigation Device of Simple Construction," Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

WOUND THERAPY SYSTEM WITH IN-LINE ORIFICE

CROSS-REFERENCE TO RELATED APPLICATIONS

This application is a U.S. National Stage entry of International Patent Application No. PCT/M2021/050619, filed Jan. 27, 2021, which claims the benefit of priority to U.S. Provisional Application No. 62/967,133, filed on Jan. 29, 2020, which is incorporated herein by reference in its entirety.

BACKGROUND

The present disclosure relates generally to a wound therapy system, and more particularly to a wound therapy system that provides negative pressure wound therapy (NPWT). NPWT refers to the creation of negative pressure (relative to atmospheric pressure) at a wound to promote healing of the wound. In a wound therapy system configured to provide NPWT, a dressing is typically sealed over a wound bed and placed in fluid communication with a pump operable to draw a negative pressure at the wound bed (i.e., in a wound space between the wound bed and the dressing). Because the dressing is sealed over the wound bed, often for a period of multiple days, it would be advantageous to determine wound volume without having to remove the dressing. In some cases, NPWT may be provided in coordination with instillation therapy and described as negative pressure and instillation wound therapy (NPIWT). Instillation therapy refers to the provision of instillation fluid (e.g., saline, antibiotic fluid, etc.) to the wound. One challenge in instillation therapy may be determining how much fluid to provide to the wound. It may be preferable to determine an amount of fluid to provide based on a size of the wound and/or a volume of available space adjacent the wound (i.e., between the dressing and the wound). Determining wound volume and instillation volume may involve use of sensors that measure an amount of air being withdrawn by the pump. Maintaining the flow of air in a laminar state for detection by the sensors may help improve the accuracy of the volume determination. Accordingly, systems and methods for maintaining a laminar flow of air for volume determination in a wound therapy system may be advantageous.

SUMMARY

One implementation of the present disclosure is a wound therapy system. The wound therapy system includes a dressing sealable over a wound and defining a wound space between the dressing and the wound, tubing comprising a first inner diameter, wherein the tubing is coupled to the dressing and fluidly communicable with the wound space, and a canister fluidly communicable with the tubing. The canister, the tubing, and the dressing define a sealed space comprising the wound space. A therapy unit is coupled to the canister and includes a pneumatic pump fluidly communicable with the sealed space, a sensor configured to measure a pressure in the sealed space, a valve positioned between the sealed space and surrounding environment and controllable between an open position and a closed position, and a control circuit. The control circuit is configured to control the pneumatic pump to remove air from the sealed space to establish a negative pressure in the sealed space, control the valve to repeatedly alternate between the open position and the closed position to allow a controlled rate of airflow through the valve, receive measurements of the pressure in the sealed space from the sensor, and determine a volume of the wound space based on the measurements of the pressure. A portion of the tubing comprises a second inner diameter that is less than the first inner diameter.

In some embodiments, the second inner diameter ranges between a first value of approximately 0.33 mm and a second value of approximately 0.43 mm.

In some embodiments, a location of the second inner diameter is between the dressing and the canister. The location of the second inner diameter can be at an interface of the canister and the tubing.

In some embodiments, a location of the second inner diameter is between the dressing and the therapy unit. The location of the second inner diameter can be at an interface of the therapy unit and the tubing.

In some embodiments, the portion of the tubing comprising the second inner diameter is structured as a disc having an aperture formed therein and disposed within a lumen of the tubing.

Another implementation of the present disclosure is an apparatus. The apparatus includes a plate having a first end coupled to a canister and a second end coupled to tubing. The plate defines a lumen having a first diameter extending between the first end and the second end. The apparatus also includes an insert having an orifice extending therethrough. The orifice defines a second diameter. The insert can be disposed at the first end of the plate such that the orifice substantially aligns with the lumen of the bellow. The apparatus also includes an overmold disposed over the insert and at least partially over a length of the plate defined between the first end and the second end. The overmold substantially secures the insert relative the bellows. The second diameter of the orifice is less than the first diameter of the lumen.

In some embodiments, the second diameter ranges between a first value of approximately 0.33 mm and a second value of approximately 0.43 mm.

In some embodiments, the insert is structured as a disc.

In some embodiments, the insert comprises a first insert end and a second insert end. An insert length measured between the first insert end and the second insert end is approximately 1.5 cm.

Another implementation of the present disclosure is a wound therapy system. The wound therapy system includes a dressing sealable over a wound and defining a wound space between the dressing and the wound, tubing comprising a first inner diameter, coupled to the dressing, and fluidly communicable with the wound space, and a canister defining a hollow volume therein and fluidly communicable with the tubing. The canister, the tubing, and the dressing define a sealed space comprising the wound space. The canister includes a canister interface configured to fluidly couple the tubing with the canister. The canister interface comprises an orifice having an interface diameter and extending from an exterior towards the hollow volume. The interface diameter is less than the first inner diameter. The wound therapy system also includes a therapy unit coupled to the canister. The therapy unit includes a pneumatic pump fluidly communicable with the sealed space, a sensor configured to measure a pressure in the sealed space, a valve positioned between the sealed space and surround environment and controllable between an open position and a closed position, and a control circuit. The control circuit is configured to control the pneumatic pump to remove air from the sealed space to establish a negative pressure in the sealed space, control the valve to repeatedly alternate between the open position and the closed position to allow a controlled rate of airflow through the valve, receive measurements of the pressure in the sealed space from the sensor, and determine a volume of the wound space based on the measurements of the pressure.

In some embodiments, the interface diameter ranges between a first value of approximately 0.33 mm and a second value of approximately 0.43 mm.

In some embodiments, the wound therapy system comprises an insert configured for placement within the interface lumen. The insert defines an orifice extending therethrough having an orifice diameter that is less than the first inner diameter. The orifice diameter can range between a first value of approximately 0.33 and a second value of approximately 0.43 mm.

Yet another implementation of the present disclosure is a method of treating a wound. The method comprises establishing a sealed space defined by a dressing, tubing having a first diameter, and a canister of a wound therapy system and comprising a wound space defined by the dressing and the wound, providing an orifice within the sealed space having a second diameter that is less than the first diameter, removing, with a pneumatic pump, air from the sealed space to establish a negative pressure in the sealed space, causing a valve to alternate between an open position and a closed position, measuring the negative pressure in the sealed space to generate pressure measurements, determining, based on the pressure measurements, a volume of the wound space, customizing a customized wound therapy based on the volume of the wound space, and providing the customized wound therapy to the wound.

In some embodiments, the second diameter ranging between a first value of approximately 0.33 mm and a second value of approximately 0.43 mm.

In some embodiments, the method involves providing the orifice via a disc defining the orifice extending therethrough.

In some embodiments, the method involves placing the disc within a lumen defined by the tubing.

In some embodiments, the method involves placing the disc within the lumen at a location between the dressing and the canister. The disc can be placed at a location of an interface of the canister and the tubing.

In some embodiments, the method involves placing the disc within the lumen at a location between the dressing and a therapy unit. The disc can be placed at a location of an interface of the therapy unit and the tubing.

In some embodiments, the method involves replacing the canister having the disc with another canister having another disc.

Yet another implementation of the present disclosure is a wound therapy system. The wound therapy system includes a dressing configured for placement over a wound, a therapy unit having a pneumatic pump operably coupled to a removable canister, tubing coupled to the dressing and the canister and defining a flowpath therethrough, and an orifice disposed within the flowpath and operable to maintain a flow through the flowpath in a laminar flow state.

In some embodiments, the orifice is disposed in a disc.

In some embodiments, the orifice is at a location on the canister at an interface of the canister and the tubing.

In some embodiments, the orifice defines an orifice diameter that ranges between a first value of 0.33 mm and 0.43 mm.

BRIEF DESCRIPTION

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION OF THE FIGURES

Overview

Referring generally to the FIGURES, a wound therapy system is shown according to various exemplary embodiments. The wound therapy system may include a therapy device and a wound dressing. The therapy device may include an instillation fluid canister, a removable fluid canister, a valve, a pneumatic pump, an instillation pump, a tubeset module, and a controller. The wound dressing can be applied to a patient's skin surrounding a wound. The therapy device can be configured to deliver instillation fluid to the wound and provide negative pressure would therapy (NPWT) by maintaining the wound at negative pressure. Components of the wound therapy device, the wound dressing, and the wound site form a negative pressure circuit.

The controller can be configured to operate the pneumatic pump, the instillation pump, the tubeset module, and/or other controllable components of the therapy device. In some embodiments, the controller estimates the volume of the wound based on a comparison of observed dynamic pressure responses to negative pressure being applied to the entirety of the negative pressure circuit and negative pressure being applied to a selected portion of the negative pressure circuit. Based on the comparison of the observed dynamic responses, the controller may be configured to determine a quantity of instillation fluid to be delivered to the wound site.

The observed dynamic pressure responses can be measured using one or more sensors. The one or more sensors are configured to measure the pressure of fluid flowing past and engaging with each sensor. Accordingly, it is desirable to maintain a smooth (e.g., laminar, restricted) flow of fluid past the sensor to provide more accurate measurements as opposed to mixed, irregular flow (e.g., turbulent flow). Disclosed herein is an orifice defining a smaller diameter (relative to tubing that couples a location of a sensor with the wound dressing) that provides a restriction to the flow of fluid through the tubing and influencing smooth, laminar, and/or restricted flow.

Wound Therapy System with In-Line Orifice

Figure 1:
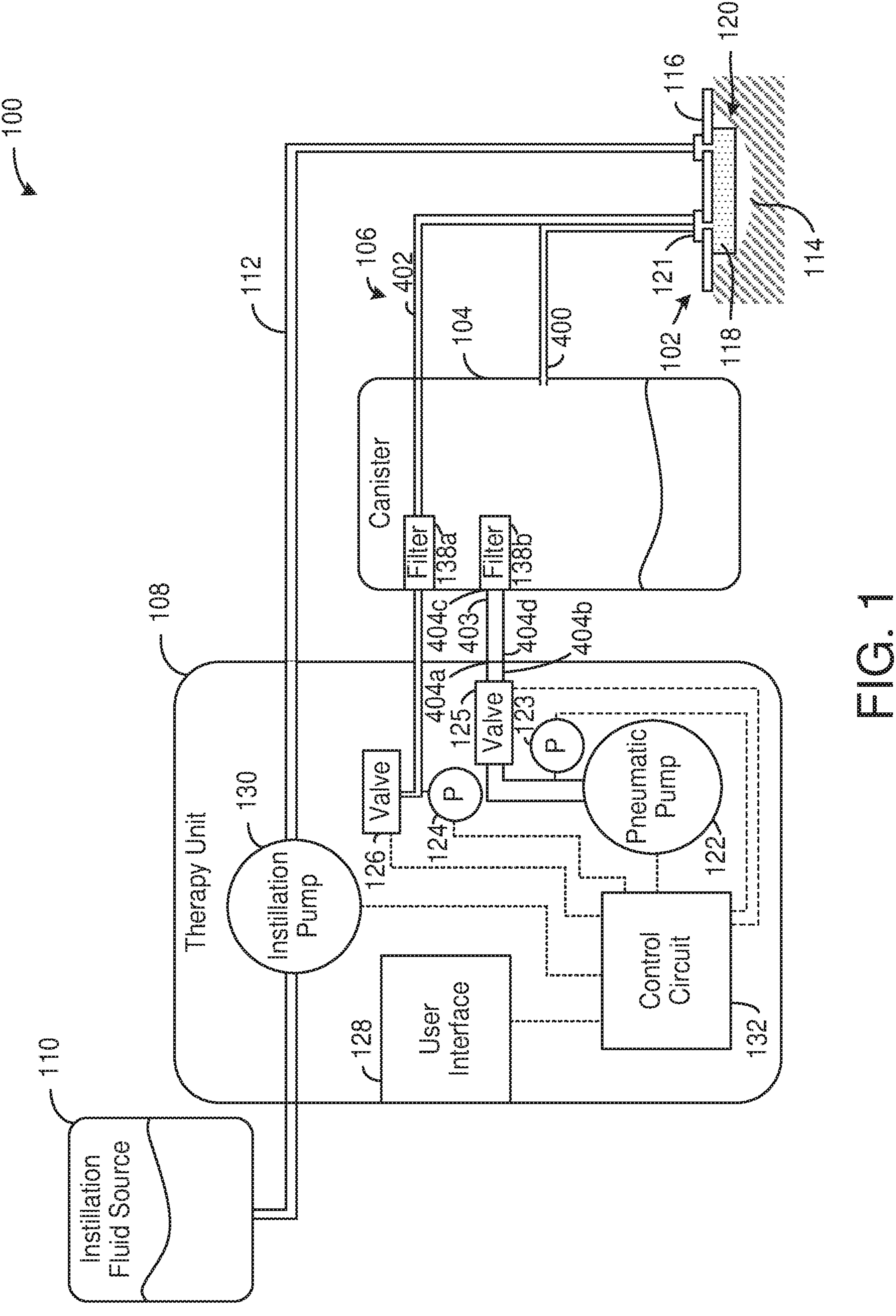
FIG. 1 is a block diagram of a negative pressure and instillation wound therapy (NPIWT) system, according to an exemplary embodiment.

Referring to FIG. 1, an NPIWT system 100 is shown, according to an exemplary embodiment. The NPIWT system 100 includes a dressing 102 fluidly communicable with a canister 104 via first tubing 106 and a therapy unit 108 coupled to the canister 104. As shown in FIG. 1, the NPIWT system 100 also includes an instillation fluid source 110 fluidly communicable with the dressing 102 via the therapy unit 108 and second tubing 112. Additionally, the NPIWT system 100 also includes a vacuum tubing 403 pneumatically coupling the canister 104 with a pneumatic pump 122.

The dressing 102 is shown as applied to a wound bed 114. The dressing 102 includes a drape 116 sealed over the wound bed 114 and a manifold layer 118 positioned between the drape 116 and the wound bed 114. In various embodiments, the dressing 102 may include various layers and features. A connection pad (e.g., low pressure interface) 121 is coupled to the drape 116 and facilitates connection of the first tubing 106 to the dressing 102. The drape 116 may be made of a substantially air-impermeable material (e.g., a polyurethane-based material) and may include an adhesive border that allows the drape to be sealed to a patient's skin around the wound bed 114. The manifold layer 118 may create a manifolding effect that allows airflow therethrough and facilitates the distribution of negative pressure across the wound bed 114. A wound space 120 that includes the open volume (i.e., through which air may flow) in the manifold layer 118 and otherwise situated between the drape 116 and the wound bed 114 is thereby established.

As described in detail with reference to FIG. 2, the vacuum tubing 403 includes an inner diameter defining a first diameter and at least one orifice 404 disposed within the vacuum tubing 403 and defining a second diameter that is smaller than the first diameter. As such, the orifice 404 provides a portion of the vacuum tubing 403 having a smaller diameter. Although described herein as an orifice disposed within a lumen of vacuum tubing 403, any other flow restrictor component providing a second diameter that is smaller than the first diameter may be used. Examples of other flow restrictor components may include, but are not limited to, a capillary insert, a flow restrictor connector, etc. Accordingly, any number of flow restrictors may be used. For example, a multi-stage flow restrictor comprising more than one flow restrictor may be used to incrementally decrease (for each individual flow restrictor) the diameter relative to the direction of flow path of the fluid through the tube. Alternatively, a flow restrictor disposed about an exterior surface of the tubing providing a second diameter that is smaller than the first diameter may be used. For example, a ring clamp may be used to engage an outer surface of the tubing and provide a decrease in diameter of the lumen of the tubing. As will be described, the second inner diameter defined by the orifice 404 provides a restriction to fluid flow through the vacuum tubing 403 and reduces turbulent flow characteristics of the fluid flowing through vacuum tubing 403. Accordingly, the second diameter provided by orifice 404 can influence flow characteristics of a fluid expelled out of the orifice 404 through an outlet provided by the orifice 404. The flow of fluid influenced by orifice 404 provides for smooth fluid travel to a first sensor 123 allowing for first sensor 123 to collect accurate data. The first sensor 123 is fluidly communicable with vacuum tubing 403 to facilitate measurement of the pressure at the wound space 120. The vacuum tubing 403 is also fluidly communicable with a first valve 125 as described below.

First tubing 106 includes an inner lumen 400 extending between the canister 104 and the drape 116 and one or more outer lumens 402 extending between therapy unit 108 and drape 116. The inner lumen 400 provides for the flow of fluid from the wound space 120 into the canister 104. The one or more outer lumens 402 are fluidly communicable with a second sensor 124. Second sensor 124 may collect similar measurements as first sensor 123. In various embodiments, NPIWT system 100 may include both first sensor 123 and second sensor 124. The one or more outer lumens 402 are also fluidly communicable with a second valve 126 as described below. It should be understood that, while described as inner and outer in the examples herein, any geometrical arrangement of multiple lumens may be used in various embodiments.

As shown in FIG. 1, orifice 404 may be located at plurality of different locations. As shown, orifice 404 is disposed in a fluid pathway defined by vacuum tubing 403 between the pneumatic pump 122 and canister 104. In some embodiments, vacuum tubing 403 includes multiple orifices 404 disposed in a series configuration between pneumatic pump 122 and canister 104. A first location is shown to locate orifice 404*a* at an interface of therapy unit 108 and vacuum tubing 403 (e.g., orifice 404 is provided by therapy unit 108). A second location is shown to locate orifice 404*b* between an interface of therapy unit 108 and vacuum tubing 403 and pneumatic pump 122 (e.g., orifice 404 is provided by vacuum tubing 403 at a location disposed within therapy unit 108). A third location is shown to locate orifice 404*c* at an interface of canister 104 and vacuum tubing 403 (e.g., orifice 404 is provided by canister 104). A fourth location is shown to locate in-line orifice 404*d* between canister 104 and therapy unit 108 (e.g., orifice 404 is provided by vacuum tubing 403 at a location disposed between canister 104 and therapy unit 108). Selection of one or more locations may be dependent upon user preference, wound therapy, wound type/characteristics, etc.

In some embodiments in which orifice 404*a* is located at an interface of therapy unit 108 and vacuum tubing 403, orifice 404*a* may be provided as a component formed monolithically within the interface of therapy unit 108. In other embodiments, orifice 404*a* may be provided as a discrete component that is configured to be installed, inserted, or otherwise disposed in the interface of therapy unit 108.

In embodiments in which orifice 404*c* is located at an interface of canister 104 and vacuum tubing 403, orifice 404*c* may be provided as a component formed monolithically within the interface of canister 104. In other embodiments, orifice 404*c* may be provided as a discrete component that is configured to be installed, inserted, or otherwise disposed in the interface of canister 104. As such, when canister 104 is removed (e.g., upon being filled with wound exudate), the orifice 404*c* is removed with the canister 104. Accordingly, replacing the original canister 104 with another canister 104 involves replacing the original orifice 404*c* with another orifice 404*c* (e.g., an orifice 404*c* formed monolithically with canister 104, an orifice 404*c* installed or disposed within the interface of canister 104).

The canister 104 is configured to collect wound exudate (e.g., fluid, other debris) removed from the wound space 120 via the first tubing 106. The canister 104 is fluidly communicable with the wound space 120 via the first tubing 106. The canister 104, the first tubing 106, and the dressing 102 thereby define a sealed space that includes the wound space 120. In some embodiments, canister 104 provides orifice 404 at an interface between vacuum tubing 403 and canister 104. Alternatively, as will be described with reference to FIGS. 3-6, canister 104 may be coupled with vacuum tubing

403 via a bellows defining a smaller diameter than the first diameter defined by vacuum tubing 403. The canister 104 is shown to include a filter 138. As shown, filter **138*a* is disposed in canister 104 and within a fluid path defined by outer lumen 402. Filter 138*b* is shown to be disposed in canister 104 and within a fluid path defined by vacuum tubing 403**.

The therapy unit 108 is pneumatically coupled to the canister 104 via vacuum tubing 403 and includes a pneumatic pump 122 fluidly communicable with the sealed space, a first sensor 123 configured and positioned to measure pressure in the sealed space, a first valve 125 positioned between the pneumatic pump and the canister 104, a user interface 128, and an instillation pump 130 coupled to the second tubing 112. The therapy unit 108 also includes a control circuit 132 communicably and operably coupled (e.g., capable of exchanging electronic signals with) the pneumatic pump 122, the first sensor 123, the first valve 125, the second sensor 124, the second valve 126, the user interface 128, and the instillation pump 130. In some embodiments, therapy unit 108 provides orifice 404 at an interface between vacuum tubing 403 and therapy unit 108. Alternatively, as will be described with reference to FIGS. 3-6, therapy unit 108 may be coupled with vacuum tubing 403 via a bellows defining a smaller diameter than the first diameter defined by vacuum tubing 403.

The pneumatic pump 122 is controllable by the control circuit 132 and operable to pump (e.g., draw, remove) air from the canister 104, the first tubing 106, and the wound space 120 (i.e., from the sealed space). The pneumatic pump 122 may thereby create a negative pressure in the sealed space relative to atmospheric pressure, for example between 25 mmHg and 175 mmHg. The pneumatic pump 122 may create a pressure differential that causes fluid and debris to be drawn out of the wound space 120, through the first tubing 106, and into the canister 104.

The first sensor 123 and the second sensor 124 are positioned and configured to measure the pressure in the sealed space. As shown in FIG. 1, the first sensor 123 is positioned to measure pressure within a fluid path defined by vacuum tubing 403 and therapy unit 108. As shown in FIG. 1, the second sensor 124 is positioned to measure pressure via one or more outer lumens 402. In other embodiments a sensor 124 may be included to measure pressure elsewhere in the sealed space (e.g., in the canister 104). As such, the location of orifice 404 (e.g., in vacuum tubing 403, at an interface of canister 104 and vacuum tubing 403, at an interface of therapy unit 108 and vacuum tubing 403) may be dependent on the location of first sensor 123. For example, assume first sensor 123 is located in canister 104. Accordingly, the orifice 404 may be located in vacuum tubing 403 and/or the interface between canister 104 and vacuum tubing 403. The first sensor 123 provides pressure measurements to the control circuit 132 (e.g., digital values, analog signals). The control circuit 132 may be configured to receive the pressure measurements from the first sensor 123 and use the pressure measurements in a control loop to generate control signals for the pneumatic pump 122 that cause the pneumatic pump 122 to maintain a desired pressure in the sealed space or provide a desired pattern of pressure in the sealed space.

The user interface 128 may include a display screen, a touch screen, a speaker, a button, a switch, or any other element capable of providing information to a user or receiving input from a user. In some embodiments, the control circuit 132 is configured to generate a graphical user interface and cause the graphical user interface to be displayed on the user interface 128. The graphical user interface may include various information about the NPIWT provided by the NPIWT system 100, for example relating to the pressure in the sealed space, an amount of instillation fluid to be provided, a schedule of negative pressure and instillation cycles, and/or a size of the wound space 120. The user interface 128 may allow a user to input commands and settings relating to the operation of the therapy unit 108. The control circuit 132 may receive such inputs from the user interface 128 and control the therapy unit 108 in accordance with the inputs.

The instillation pump 130 is configured to cause instillation fluid to be transported from the instillation fluid source 110 to the wound space 120 via second tubing 112. The instillation pump 130 may be controllable by the control circuit 132 to provide a desired amount of the instillation fluid to the wound space 120, provide instillation fluid to the wound space 120 at a desired rate, prevent instillation fluid from flowing to the wound space 120, or otherwise control the flow of instillation fluid to the wound space 120. The instillation pump may include a peristaltic pump or some other type of pump.

The first valve 125 and second valve 126 are controllable between an open position and a closed position. As shown in FIG. 1, the first valve 125 and the second valve 126 are located at an interior of the therapy unit 108. The second valve 126 is also shown as communicable with the one or more outer lumens 402 of the first tubing 106. Although FIG. 1 illustrates system 100 having two valves (i.e., first valve 125 and second valve 126), it is understood that any number of valves may be included in system 100. For example, system 100 may include two valves (disposed in a series configuration) operating in a chatter configuration (e.g., simultaneously opening and closing, alternatively opening and closing). The first valve 125 and the second valve 126 may also be controllable to allow a controlled rate of airflow therethrough to facilitate determination of a volume of the wound space 120.

The control circuit 132 is configured to control the operation of the therapy unit 108. For example, as described in detail below, the control circuit 132 is configured to control the pneumatic pump 122 to remove air from the sealed space to establish a negative pressure in the sealed space, control the first valve 125 to provide a controlled leak to the sealed space, receive pressure measurements from the first sensor 123, determine a volume of the wound space 120 based on the pressure measurements, and customize a wound therapy based on the volume of the wound space 120. Although the control circuit 132 is described herein as to determine a volume of the wound space 120, the control circuit 132 may additionally, or alternatively, use the pressure measurements to determine a rate of dwell therapy, a frequency of periodic instillation therapy, or a volume of constant stream instillation. Accordingly, although the system is described herein as applying an instillation fluid, any other fluid (e.g., collagen) may be used.

Figure 2:
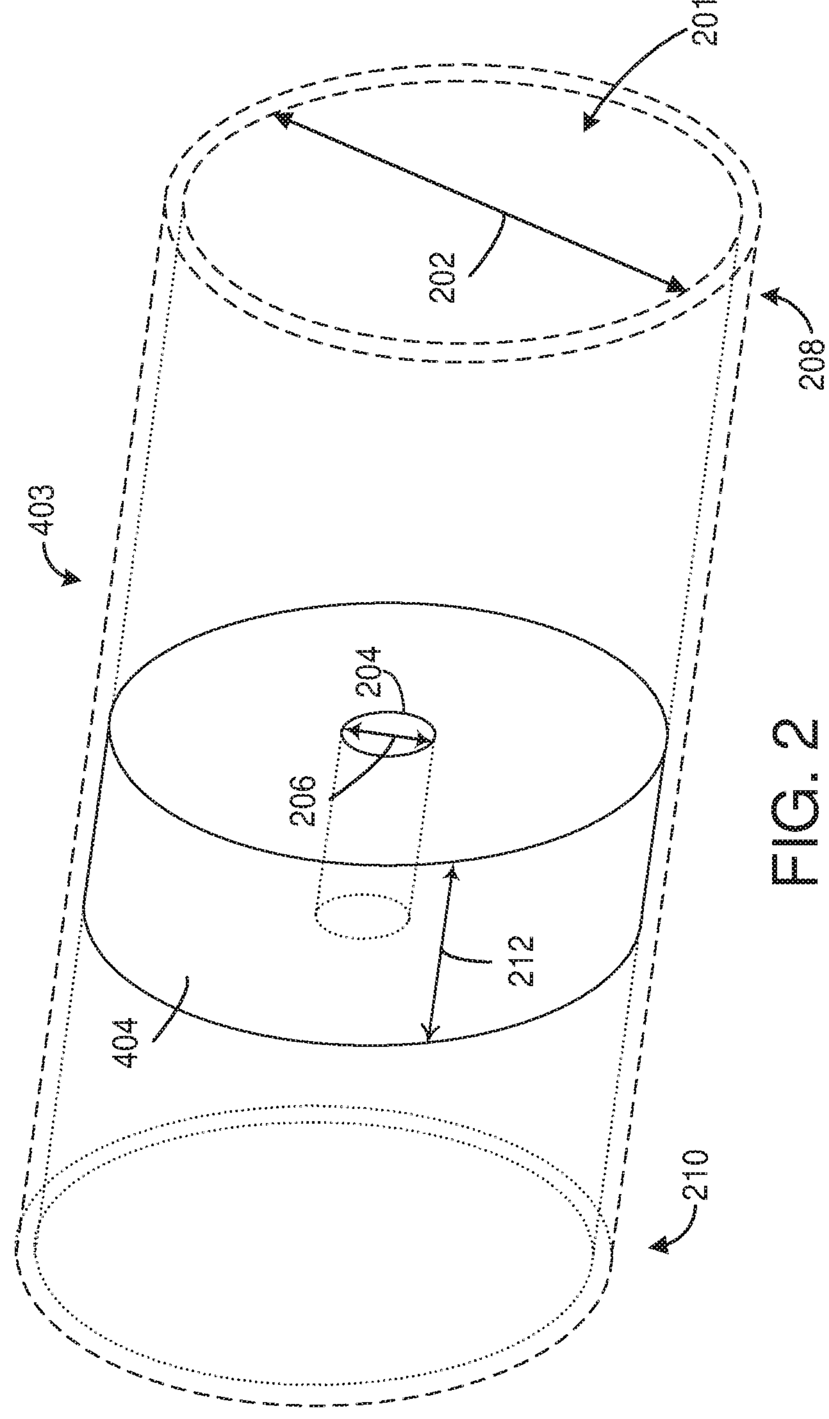
FIG. 2 is a perspective illustration of an orifice of the tubing of the NPIWT system of FIG. 1, according to an exemplary embodiment.

Referring now to FIG. 2, a perspective view of a section of the vacuum tubing 403 including orifice 404 is shown, according to an exemplary embodiment. In the embodiment shown, the vacuum tubing 403 includes a vacuum lumen 201 defining a first inner diameter 202. Although FIG. 2 shows vacuum tubing 403 including vacuum lumen 201, it should be understood that the features disclosed herein may be used with one or more other lumens (e.g., outer lumen 402, inner lumen 400). The size of first inner diameter 202 may be configurable based on factors such as therapy unit configuration, wound characteristics (e.g., size, location), etc. Vacuum tubing 403 is also shown to include orifice 404 disposed within the vacuum lumen 201 of vacuum tubing 403. The orifice 404 may be included as a discrete component that is installed within the vacuum lumen 201 of vacuum tubing 403. For example, orifice 404 may be structured as a discrete disc component that is installed within the vacuum lumen 201. In such embodiments, various adhesive operations (e.g., applying adhesive, press fitting) may be used to secure a location of orifice 404 within vacuum lumen 201. Alternatively, orifice 404 may be provided as a component that is formed monolithically with vacuum tubing 403.

Orifice 404 is shown to include an orifice lumen 204 extending therethrough and defining a second inner diameter 206. The orifice lumen 204 extends through the orifice 404 such that a first end 208 of vacuum tubing 403 is in fluid communication with a second end 210 of vacuum tubing 403 that extends in an opposite direction of the first end 208. The second inner diameter 206 is smaller than the first inner diameter 202 and may be configurable based on factors such as tubing size, therapy unit parameters, wound treatment parameters, etc. In some embodiments, the second inner diameter 206 ranges between a first value of approximately 0.1 mm and a second value of 1.0 mm. In some embodiments, the second inner diameter 206 ranges between a first value of approximately 0.2 mm and a second value of 0.75 mm. In some embodiments, the second inner diameter 206 ranges between a first value of approximately 0.33 mm and a second value of approximately 0.43 mm. In some embodiments, the second inner diameter 206 is approximately 0.38 mm. Orifice 404 is also shown to have a length 212 extending along outer lumen 402. In various arrangements, the size of second inner diameter 206 is related to a size (e.g., volume, cross-section, thickness, length) of filter 138. The size of length 212 may be less than a length of vacuum tubing 403 (not shown). Accordingly, the size of length 212 may be customizable based on factors such as therapy unit parameters, wound size, etc.

Figure 4:
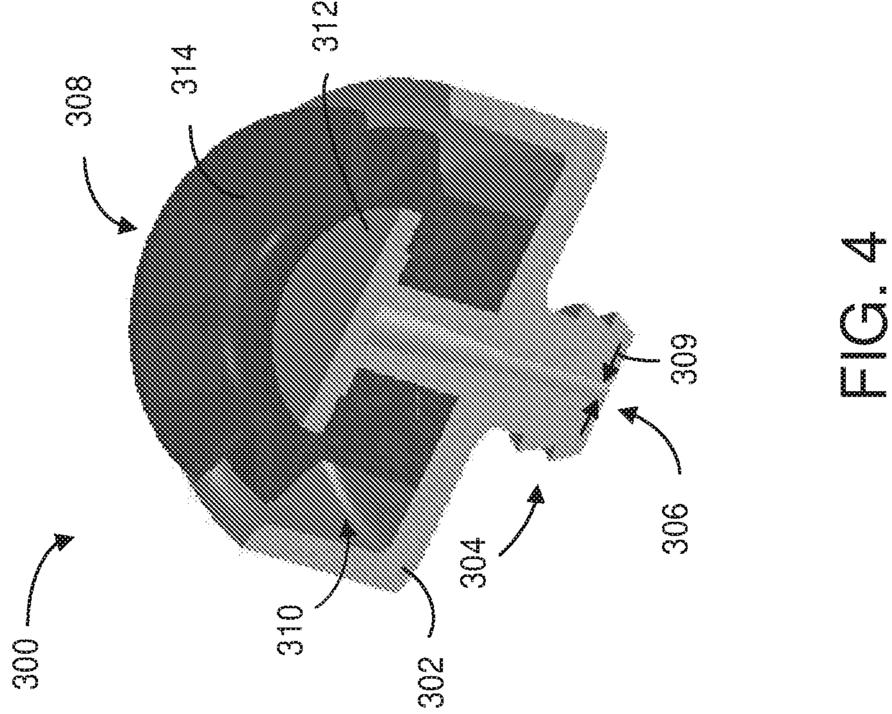
FIG. 4 is a cross-sectional illustration of the bellows of FIG. 3, according to an exemplary embodiment.
Figure 3:
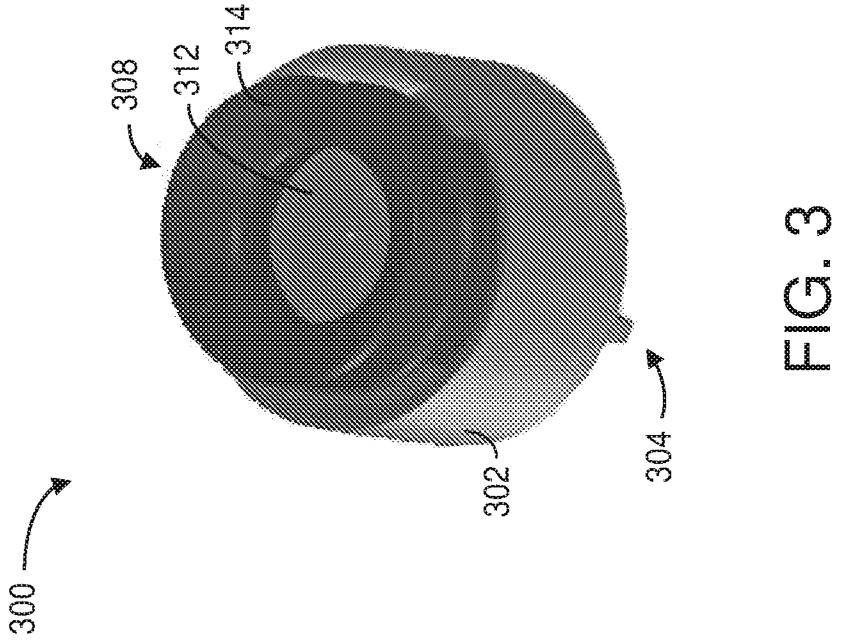
FIG. 3 is a perspective illustration of a bellows of the NPIWT system of FIG. 1, according to an exemplary embodiment.

Referring now to FIGS. 3 and 4, a second embodiment of the orifice 404 is shown as a bellows 300, according to an exemplary embodiment. In such embodiments, bellows 300 provides an interface between vacuum tubing 403 and canister 104 or therapy unit 108. As shown in FIG. 4, bellows 300 includes a plate 302. Plate 302 is configured to attach the bellows 300 to vacuum tubing 403 via a first end 304. First end 304 may provide various attachment features (e.g., adhesive material, threaded structure, snap-fit structure, deforming, outwardly-extending flanges) configured to secure the bellows 300 to the tubing. Plate 302 is shown to include a plate lumen 306 extending between the first end 304 and a second end 308 and configured to fluidly couple the vacuum tubing 403 with canister 104 or therapy unit 108. Plate lumen 306 is shown to define a plate lumen diameter 309. In some embodiments, the plate lumen diameter 309 is approximately 3 mm. Plate 302 is also shown to include a receiving volume 310 within which an insert 312 and an overmold 314 are placed, according to an example embodiment. Insert 312 is disposed at the first end 304 between the plate 302 and the overmold 314 such that an insert lumen defined by the insert 312 aligns with the plate lumen 306. The overmold 314 is disposed over the insert 312 and at least a partially over a length of the plate 302 defined between first end 304 and second end 308. The overmold 314 is configured to engage the insert 312 and the plate 302 securing the insert relative the plate 302.

Figure 5:
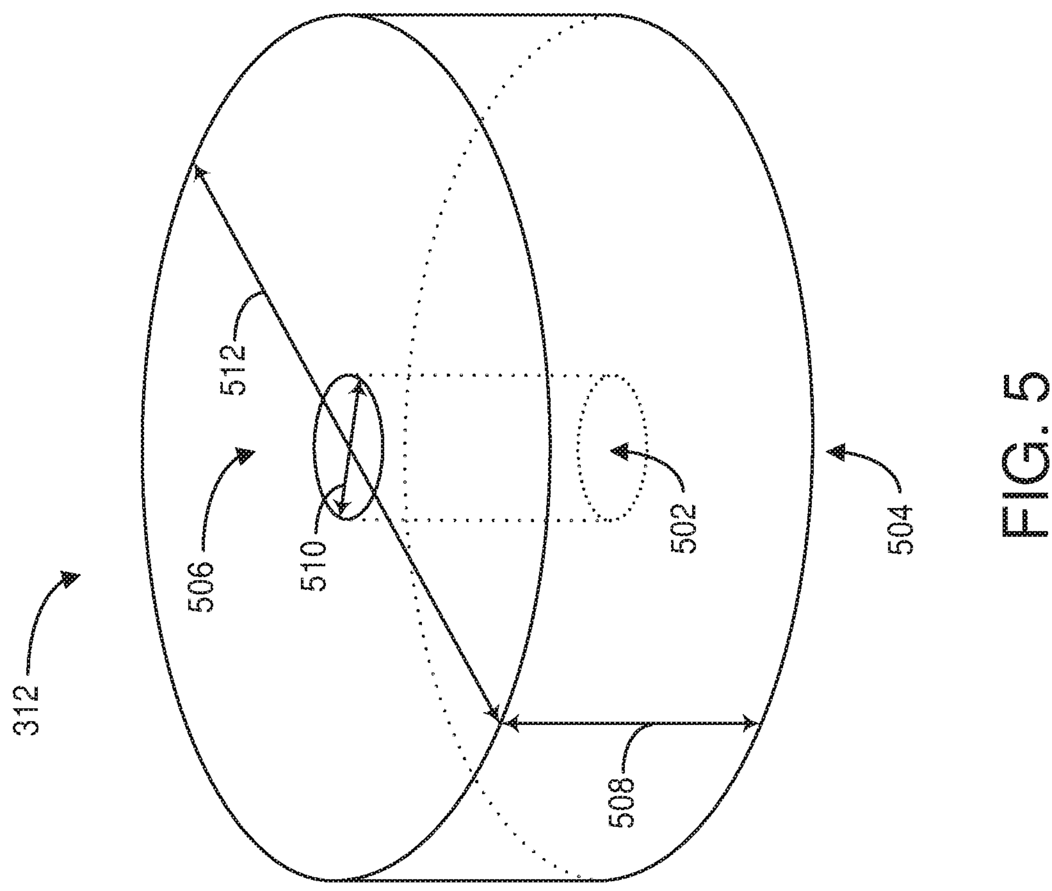
FIG. 5 is a perspective illustration of an insert used in the bellows of FIGS. 3 and 4, according to an exemplary embodiment.

Referring now to FIG. 5, insert 312 is shown, according to an example embodiment. In some embodiments, insert 312 is structured as a disc. Insert 312 is shown to include an insert lumen 502 extending therethrough between a first insert end 504 and a second insert end 506 and configured to fluidly couple the plate lumen 306 with a canister (e.g., canister 104) or a therapy unit (e.g., therapy unit 108). In some embodiments, an insert length 508 defined between the first insert end 504 and the second insert end 506 is approximately 1.5 cm. Insert 312 is configured for placement within the receiving volume 310 of plate 302 and to provide a restriction to fluid flow received from the plate lumen 306. Accordingly, insert lumen 502 is fluidly communicable with plate lumen 306. Insert lumen 502 is shown to define an insert diameter 510. In some embodiments, insert diameter 510 is smaller than plate lumen diameter 309. In some embodiments, the insert diameter 510 ranges between a first value of approximately 0.1 mm and a second value of 1.0 mm. In some embodiments, the insert diameter 510 ranges between a first value of approximately 0.2 mm and a second value of 0.75 mm. In some embodiments, insert diameter 510 is ranges between approximately 0.33 mm and 0.43 mm. The insert diameter 510 defined by insert lumen 502 influences flow characteristics of a fluid expelled out of the plate lumen 306 to the insert lumen 502. The flow characteristics influenced by insert 312 provides for smooth fluid travel to first sensor 123 allowing for first sensor 123 to collect accurate data. The insert 312 is also shown to define an outer diameter 512. In some embodiments, outer diameter 512 is approximately 8 mm.

Figure 6:
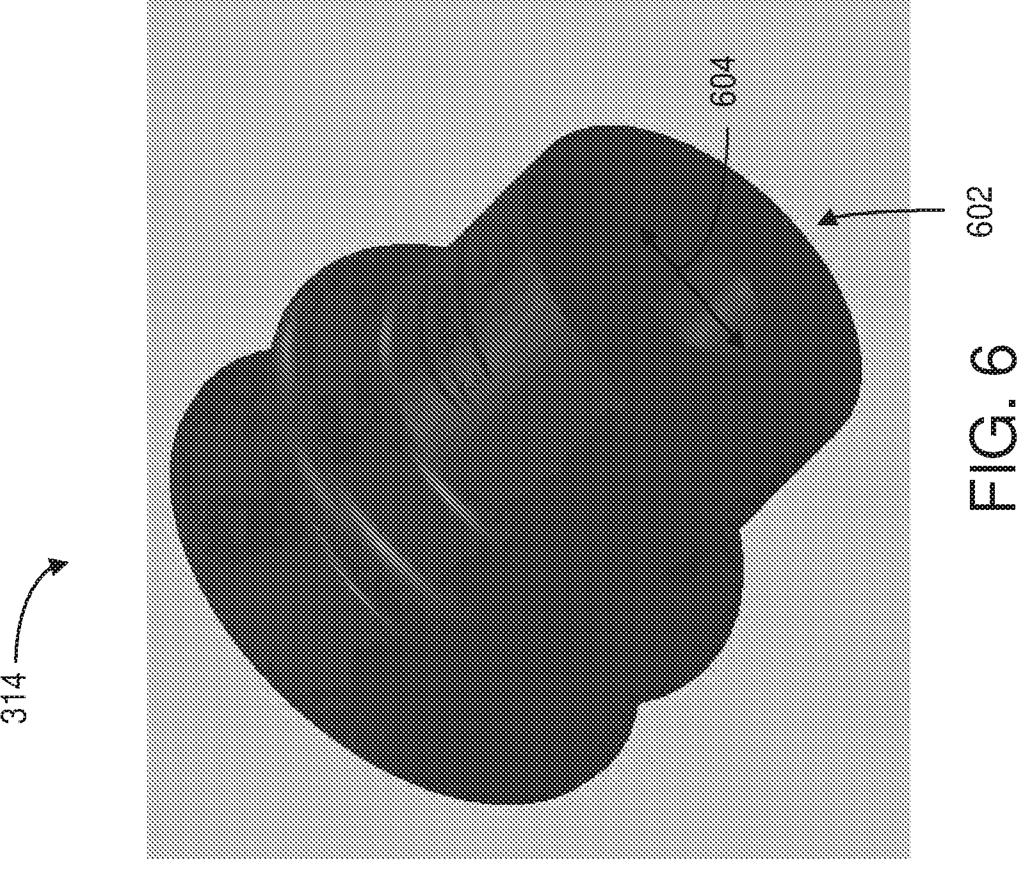
FIG. 6 is a perspective illustration of an overmold used in the bellows of FIGS. 3 and 4, according to an exemplary embodiment.

Referring now to FIG. 6, overmold 314 is shown, according an example embodiment. Overmold 314 is configured to sealably couple the plate 302 with canister 104 or therapy unit 108. In some embodiments, overmold 314 is configured to engage plate 302 and insert 312 to secure a location of the insert 312 relative the plate 302 and overmold 314. Overmold 314 is shown to include an overmold lumen 602 extending therethrough and configured to fluidly couple the insert lumen 502 with canister 104 or therapy unit 108. Overmold lumen 602 is shown to define an overmold diameter 604 that is larger than insert diameter 510. In some embodiments, overmold diameter 604 is approximately 3 mm.

Figure 7:
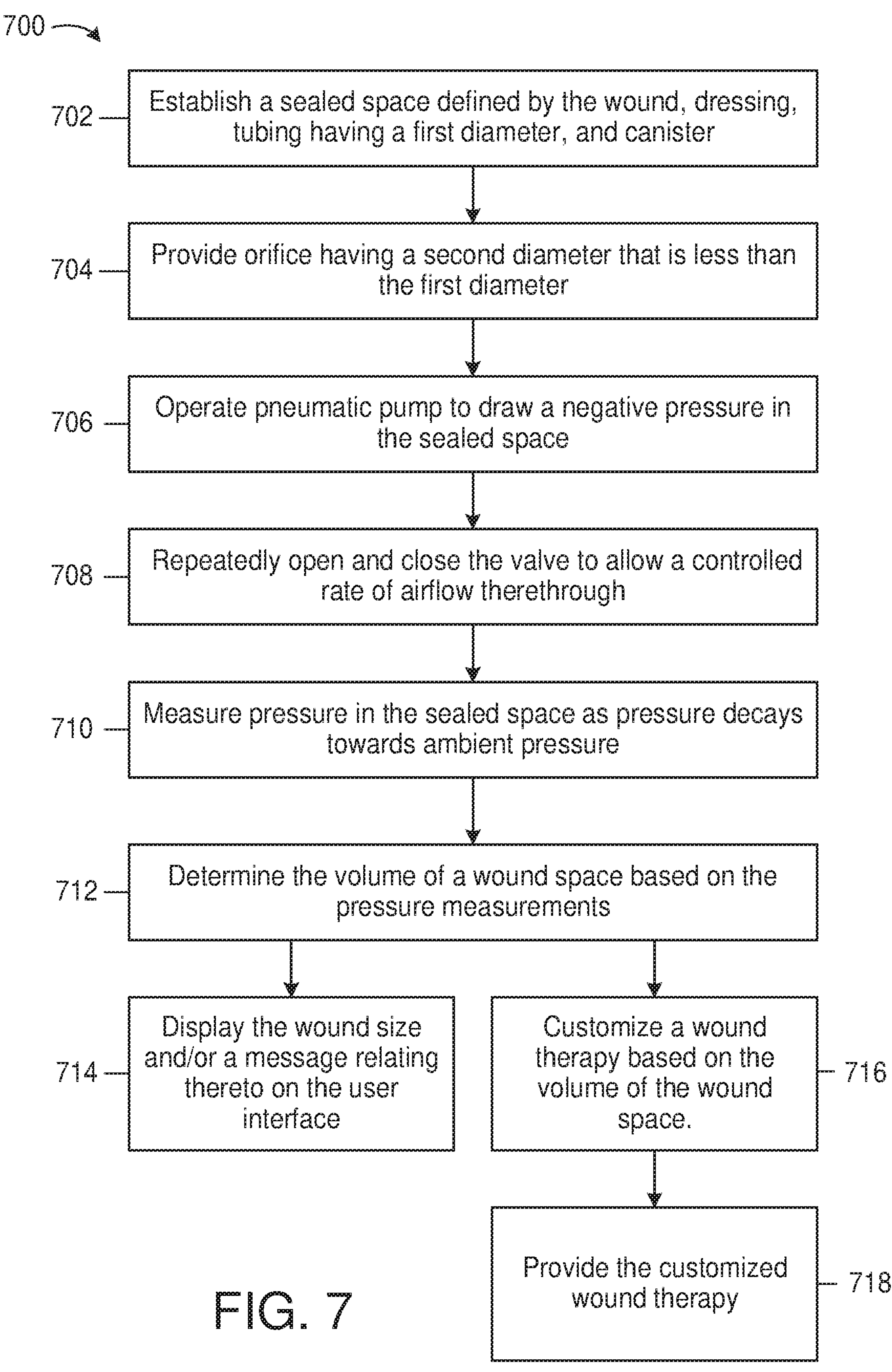
FIG. 7 is a flowchart illustrating a process of providing a customized wound therapy using the NPIWT system of FIG. 1, according to an exemplary embodiment.

Referring now to FIG. 7, a flowchart of a process 700 for wound volume determination and wound therapy customization is shown, according to an exemplary embodiment. The process 700 may be carried out by the NPIWT system 100 of FIG. 1.

At step 702, a sealed space defined by the wound bed 114, the dressing 102, the first tubing 106, and the canister 104 is established. The sealed space includes the wound space 120. In other words, the dressing 102 is applied to the wound bed 114 with the drape 116 sealed over the wound bed 114 and the manifold layer 118 (or other layers included in the dressing 102 in various embodiments) to define the wound space 120. The first tubing 106 is coupled to the drape 116 in fluid communication with the wound space 120 via the connection pad 121, The first tubing 106 is also coupled to the canister 104 in fluid communication with the canister 104 or therapy unit 108. The first tubing 106 also defines a lumen having first inner diameter 202 extending therethrough.

At step 704, orifice 404 having a second inner diameter 206 that is less than the first inner diameter 202 is provided. In some embodiments, the second inner diameter 206 ranges between a first value of approximately 0.1 mm and a second value of 1.0 mm. In some embodiments, the second inner diameter 206 ranges between a first value of approximately 0.2 mm and a second value of 0.75 mm. In some embodiments, the second inner diameter 206 ranges between approximately 0.33 mm and 0.43 mm. In some embodiments, orifice 404 may be provided as a discrete disc component defining the orifice lumen 204 extending therethrough and configured for placement within the lumen of the vacuum tubing 403. Alternatively, the orifice 404 may be provided as a component formed monolithically with the vacuum tubing 403. The orifice 404 may be located at various locations such as between the therapy unit 108 and the canister 104, at an interface of the vacuum tubing 403 and the canister 104, within the therapy unit 108, or at an interface of the therapy unit 108 and the vacuum tubing 403. In some embodiments, orifice 404 may be structured as bellows 300 configured to fluidly and sealably couple the vacuum tubing 403 with the canister 104 or the therapy unit 108.

At step 706, the pneumatic pump 122 is operated to draw a negative pressure in the sealed space. That is, the control circuit 132 provides a control signal to the pneumatic pump 122 that causes the pneumatic pump to remove air from the sealed space. The control circuit 132 may receive pressure measurements from first sensor 123 and cause the pneumatic pump 122 to cease operation when a desired negative pressure is achieved (e.g., −125 mmHg) and/or otherwise control the pneumatic pump 122 based on the pressure measurements to provide a desired negative pressure or pattern of desired negative pressures.

At step 708, the first valve 125 is repeatedly opened and closed (e.g., "cycled") to allow a controlled rate of airflow therethrough. The control circuit 132 may provide a control signal to the first valve 125 that causes the first valve 125 to repeatedly open and close. For example, in an embodiment where the first valve 125 is a solenoid valve, the control circuit 132 provides a voltage pattern to the first valve 125. That is, the control circuit 132 may repeatedly alternate a voltage differential across between a positive lead and a negative lead between approximately zero volts and a non-zero voltage (e.g., approximately five volts). For example, the voltage pattern may include a step function that repeatedly steps between approximately zero voltage and the non-zero voltage.

At step 710, the pressure in the sealed space is measured as the negative pressure in the sealed space decays towards ambient pressure (i.e., approaches approximately atmospheric pressure). The controlled airflow through the first valve 125 allows air to enter the sealed space and causes the pressure in the sealed space to decay towards ambient pressure. The first sensor 123 may measure the pressure in the sealed space and provide the pressure measurements to the control circuit 132. The control circuit 132 may record (store, save) the pressure measurements. In some embodiments, the control circuit 132 may collect the pressure measurements to form a pressure decay curve.

At step 712, the volume of the wound space 120 is determined based on the pressure measurements. For example, based on the known controlled rate of airflow through the first valve 125 and the measured pressure decay curve, the volume of the sealed space may be determined. The volume of the wound space may then be determined by removing a volume of the canister and tube from the total volume of the sealed space. In some cases, one or more additional valves, sensors, etc. are included to facilitate generation and collection of data for use in wound size determination. Various methods for calculating wound size are described in U.S. Patent Application No. 62/802,034 filed Feb. 6, 2019, incorporated by reference herein in its entirety.

At step 714, the wound size (e.g., the volume of the wound space 120) and/or a message relating thereto is displayed on the user interface 128. For example, the control circuit 132 may cause a graphical user interface that includes the wound size to be displayed on a screen of the user interface 128. As another example, the control circuit 132 may determine one or more warnings, progress reports, or other wound-related message based on the wound size and control the user interface 128 to display the warning, report, or other message. For example, the user interface 128 may display a graphical representation of change in the volume of the wound space over time.

At step 716, a wound therapy is customized based on the volume of the wound space. In some embodiments, the control circuit 132 automatically customizes a wound therapy based on the determined volume of the wound space 120. In other embodiments, a user is facilitated in customizing a wound therapy based on the volume of the wound space 120 based on information displayed on the user interface 128.

In the example shown, the control circuit 132 automatically customizes instillation by automatically determining an amount of instillation fluid to be supplied to the wound space 120 based on the determined volume of the wound space 120. For example, the control circuit 132 may multiply the determined volume of the wound space 120 by a scaling factor to determine the amount of instillation fluid to be supplied to the wound space 120. As another example, the control circuit 132 may determine the amount of instillation to be supplied as equal to the volume of the wound space 120. Various calculations are possible for various applications, wound types, instillation fluid types, patient and/or caregiver preferences, etc.

At step 718, the customized wound therapy is provided. For example, the control circuit 132 may control the instillation pump 130 to provide the determined amount of instillation fluid from the instillation fluid source 110 to the wound space 120. Instillation therapy may thereby be tailored to meet the needs of the healing wound in real time. Various other customized therapies are possible in various embodiments.

Configuration of Exemplary Embodiments

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure. Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A wound therapy system, comprising:

a dressing sealable over a wound and defining a wound space;

a conduit comprising a first inner diameter, wherein the conduit is fluidly communicable with the wound space;

a canister fluidly communicable with the conduit, wherein the canister, the conduit, and the dressing define a sealed space comprising the wound space;

a therapy unit coupled to the canister and comprising:

a pneumatic pump fluidly communicable with the sealed space;

a sensor configured to measure a pressure in the sealed space;

a valve positioned between the sealed space and surrounding environment and controllable between an open position and a closed position; and a control circuit configured to:

control the pneumatic pump to remove air from the sealed space to establish a negative pressure in the sealed space;

receive measurements of the pressure in the sealed space from the sensor; and determine a volume of the wound space based on the measurements of the pressure; and a bellows fluidly communicable with the pneumatic pump and the canister, the bellows comprising:

a plate having a first end and a second end, wherein the plate defines a plate lumen having a plate lumen diameter extending between the first end and the second end;

an insert defining an insert lumen extending through the insert and having an insert lumen diameter, wherein the insert lumen diameter is less than the plate lumen diameter, and wherein the insert is disposed at the first end of the plate such that the insert lumen aligns with the plate lumen; and an overmold disposed over the insert and at least partially over a length of the plate defined between the first end and the second end of the plate, wherein the overmold substantially secures the insert relative the plate.

2. The wound therapy system of claim 1, wherein the conduit is coupled to the dressing, and wherein the overmold is configured to sealably couple the plate with the canister.

3. The wound therapy system of claim 1, wherein a location of the bellows is between the dressing and the therapy unit and the overmold is configured to sealably couple the plate with the therapy unit.

4. The wound therapy system of claim 1, wherein the control circuit is further configured to control the valve to repeatedly alternate between the open position and the closed position to allow a controlled rate of air flow through the valve, wherein the control circuit is further configured to determine a pressure decay curve based on the measurements of the pressure.

5. The wound therapy system of claim 1, wherein the insert lumen diameter ranges between a first value of approximately 0.1 mm and a second value of approximately 1.0 mm.

6. The wound therapy system of claim 1, wherein the valve is positioned between the pneumatic pump and the canister.

7. The wound therapy system of claim 1, wherein the bellows is positioned between the pneumatic pump and the canister.

8. The wound therapy system of claim 1, wherein the control circuit is further configured to determine an amount of instillation fluid to be supplied to the wound space from an instillation fluid source based on the determined volume of the wound space.

9. The wound therapy system of claim 1, wherein the insert lumen diameter ranges between a first value of approximately 0.33 mm and a second value of approximately 0.43 mm.

10. A wound therapy system, comprising:

a dressing configured for placement over a wound;

a therapy unit having a pneumatic pump operably coupled to a removable canister;

a conduit coupled to the dressing and the canister and defining a flowpath therethrough; and a bellows disposed within the flowpath and operable to maintain a restriction to a flow through the flowpath, the bellows comprising:

a plate defining a plate lumen having a plate lumen diameter;

an insert defining an insert lumen having an insert lumen diameter, wherein the insert lumen diameter is less than the plate lumen diameter, and wherein the insert lumen is aligned with the plate lumen; and an overmold disposed over the insert and at least partially over a length of the plate, wherein the overmold substantially secures the insert relative the plate.

* * * * *